(12) United States Patent
Stafslien et al.

(10) Patent No.: US 8,283,432 B2
(45) Date of Patent: *Oct. 9, 2012

(54) SILOXANE POLYMER CONTAINING TETHERED FLUOROQUINOLONE

(75) Inventors: Shane Jeremy Stafslien, West Fargo, ND (US); Bret Ja Chisholm, West Fargo, ND (US); Alex J. Kugel, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/284,527

(22) Filed: Oct. 28, 2011

(65) Prior Publication Data

US 2012/0046313 A1 Feb. 23, 2012

Related U.S. Application Data

(63) Continuation of application No. 12/378,049, filed on Feb. 10, 2009, now Pat. No. 8,071,706.

(60) Provisional application No. 61/065,577, filed on Feb. 13, 2008.

(51) Int. Cl.
*C08G 77/04* (2006.01)
*C08G 77/12* (2006.01)
*A61F 2/00* (2006.01)

(52) U.S. Cl. ............................. 528/26; 528/31; 424/423
(58) Field of Classification Search ........................ None
See application file for complete search history.

(56) References Cited

U.S. PATENT DOCUMENTS

| | | | |
|---|---|---|---|
| 4,125,491 A | 11/1978 | Gorman | |
| 4,298,543 A | 11/1981 | Law et al. | |
| 4,902,767 A | 2/1990 | Roitman et al. | |
| 4,910,252 A | 3/1990 | Yonehara et al. | |
| 5,179,148 A | 1/1993 | Inoue et al. | |
| 5,203,991 A | 4/1993 | Kutsuna et al. | |
| 5,237,082 A | 8/1993 | Leir et al. | |
| 5,986,018 A | 11/1999 | Yamaguchi et al. | |
| 6,369,186 B1 | 4/2002 | Branlard et al. | |
| 6,387,997 B1 | 5/2002 | Grolemund et al. | |
| 6,413,446 B1 | 7/2002 | Mechtel et al. | |
| 6,458,878 B1 | 10/2002 | Tsuboi et al. | |
| 6,482,912 B2 | 11/2002 | Boudjouk et al. | |
| 6,500,549 B1 | 12/2002 | Deppisch et al. | |
| 6,524,564 B1 | 2/2003 | Kim et al. | |
| 6,861,493 B2 | 3/2005 | Bauer et al. | |
| 7,345,131 B2 | 3/2008 | Selbertinger et al. | |
| 7,449,537 B2 | 11/2008 | Boudjouk et al. | |

(Continued)

FOREIGN PATENT DOCUMENTS

CA 2 413 672 A1 8/2003

(Continued)

OTHER PUBLICATIONS

Spoering et al., J. Bacteriology, 2001, 183(23), pp. 6746-6751.*

(Continued)

*Primary Examiner* — Brian Gulledge
(74) *Attorney, Agent, or Firm* — Foley & Lardner LLP

(57) ABSTRACT

A polymer that is a polysiloxane polymer has fluoroquinolone antibiotic groups, or pharmaceutically acceptable salts thereof, attached via linkers. The linkers may be hydrolytically labile thereby providing a manner of releasing the fluoroquinolone antibiotic from the polymer.

25 Claims, 5 Drawing Sheets

U.S. PATENT DOCUMENTS

| | | | |
|---|---|---|---|
| 7,452,956 | B2 | 11/2008 | Cheng et al. |
| 7,544,722 | B2 | 6/2009 | Boudjouk et al. |
| 2003/0022793 | A1 | 1/2003 | Ring et al. |
| 2003/0129421 | A1 | 7/2003 | Terauchi et al. |
| 2003/0207962 | A1 | 11/2003 | Oya et al. |
| 2003/0236552 | A1 | 12/2003 | Roby |
| 2005/0003216 | A1* | 1/2005 | Frances et al. ............. 428/447 |
| 2005/0129962 | A1 | 6/2005 | Amidaiji et al. |
| 2005/0227092 | A1 | 10/2005 | Yamaya et al. |
| 2006/0014015 | A1 | 1/2006 | Travelute et al. |
| 2006/0223969 | A1 | 10/2006 | Roesler et al. |
| 2006/0252094 | A1 | 11/2006 | Zhou et al. |
| 2007/0021529 | A1 | 1/2007 | Boudjouk et al. |
| 2007/0032626 | A1 | 2/2007 | Roesler et al. |
| 2007/0042199 | A1 | 2/2007 | Chisholm et al. |
| 2007/0048344 | A1 | 3/2007 | Yahiaoui et al. |
| 2007/0112161 | A1 | 5/2007 | Roesler et al. |
| 2007/0112164 | A1 | 5/2007 | Roesler et al. |
| 2007/0129474 | A1 | 6/2007 | Salamone et al. |
| 2007/0132949 | A1 | 6/2007 | Phelan |
| 2007/0255004 | A1 | 11/2007 | Lohrmann et al. |
| 2008/0181862 | A1 | 7/2008 | Chisholm et al. |
| 2008/0213599 | A1 | 9/2008 | Webster et al. |
| 2009/0018276 | A1 | 1/2009 | Boudjouk et al. |
| 2009/0111937 | A1 | 4/2009 | Webster et al. |
| 2010/0204399 | A1 | 8/2010 | Chisholm et al. |
| 2010/0280148 | A1 | 11/2010 | Webster et al. |

FOREIGN PATENT DOCUMENTS

| | | |
|---|---|---|
| CA | 2 621 000 A1 | 3/2007 |
| EP | 1 496 079 B1 | 7/2005 |
| WO | WO 2005-030405 A2 | 4/2005 |
| WO | WO 2006-086092 A2 | 8/2006 |
| WO | WO 2006/121937 * | 11/2006 |
| WO | WO 2006-121937 A1 | 11/2006 |
| WO | WO 2007/053163 A2 | 5/2007 |
| WO | WO 2008-008077 A2 | 1/2008 |
| WO | WO 2008/127489 A2 | 10/2008 |
| WO | WO 2009-025924 A2 | 2/2009 |

OTHER PUBLICATIONS

U.S. Appl. No. 12/378,155, filed Feb. 11, 2009, Chisholm et al.
Abstract for Japanese Publication No. JP 63-277222 A, "Curing Resin," Murata Tsutomu et al., date of publication Nov. 15, 1998 (1 pg.).
Abstract for JP 03-327912, "Primer Antifouling Coating Material Composition for Ship, Composite Antifouling Coating Film for Ship, Method for Forming the Composite Antifouling Coating Film, Ship Coated with the Composite Antifouling Coating Film and Antifouling Method for Outer Hull of Ship," Masuda Hiroshi et al., publication date Nov. 19, 2003 (1 pg.).
Abstract for JP 04-370163, "Coating Composition," Masuoka Shigeru et al., publication date Dec. 22, 1992 (1 pg.).
Abstract for JP 2007246576 (A), "Water Paint Composition", Matsushita et al., publication date Sep. 27, 2007 (1 pg.).
Abstract for JP 2-47371 A, Kiyoueishiya Yushi Kagaku Kogyo KK, publication date Feb. 16, 1990 (2 pgs.).
Abstract for JP 53-139653, "Marine Antifouling Material," Takamizawa Minoru et al., publication date Dec. 6, 1978 (1 pg.).
Abstract for JP 63-270738, "Polyamine/Polysiloxane Block Copolymer," Tezuka Yasushi et al., publication date Nov. 8, 1988 (1 pg.).
BALL, "Efficacy and Safety of Levofloxacin in the Context of Other Contemporary Fluoroquinolones: A Review", *Current Therapeutic Research®*, vol. 64, No. 9, Nov./Dec. 2003 (pp. 646-661).
Cassé et al., "Laboratory screening of coating libraries for algal adhesion," *Biofouling*, 2007, 23(3/4) (pp. 267-276).
Chen et al., "Solvent Effects on the Surface Composition of Poly(dimethylsiloxane)-co-Polystyrene-Polystyrene Blends," Macromolecules, vol. 31, No. 26, 1998 (pp. 9328-9336).
Dizman et al., "Synthesis, Characterization, and Antibacterial Activities of Novel Methacrylate Polymers Containing Norfloxacin", *Biomacromolecules*, vol. 6, No. 1, 2005 (pp. 514-520).
Ekin et al., "Library Synthesis and Characterization of 3-Aminopropyl-Terminated Poly(dimethylsiloxane)s and Poly($\epsilon$-caprolactone)-b-Poly(dimethylsiloxane)s," *Journal of Polymer Science: Part A: Polymer Chemistry*, 2006, vol. 44(16) (pp. 4880-4894).
Ekin et al., "Synthesis and Characterization of Novel Hydroxyalkyl Carbamate and Dihydroxyalkyl Carbamate Terminated Poly(dimethylsiloxane) Oligomers and Their Block Copolymers with Poly($\epsilon$-caprolactone)," *Macromolecules*, 2006, 39(25) (pp. 8659-8668).
Ekin et al., "Synthesis, formulation, and characterization of siloxane-polyurethane coatings for underwater marine applications using combinatorial high-throughput experimentation," *J. Coat. Technol. Res.*, 2007, 4(4) (pp. 435-451).
Ekin et al., Combinatorial and High-Throughput Screening of the Effect of Siloxane Composition on the Surface Properties of Crosslinked Siloxane—Polyurethane Coatings, *J. Comb. Chem.*, 2007, 9(1) (pp. 178-188).
Francolini et al., "Polymer designs to control biofilm growth on medical devices", *Reviews in Environmental Science and Bio/Technology*, vol. 2, 2003 (pp. 307-319).
Ha et al., Journal of Macromolecular Science, Polymer Reviews, 2005, C45, 32 pages.
Ho et al., "Polydimethylsiloxane-Urea-Urethane Copolymers with 1,4-Benzenedimethanol as Chain Extender," Macromolecules, vol. 26, No. 25, 1993 (pp. 7029-7036).
Holohan et al., "Monofunctional polydimethylsiloxane oligomers for graft copolymerization," Macromol. Chem. Phys., Volume-Issue 195, 1994 (pp. 2965-2979) 16 pgs. total with cover pg.
Iojoiu et al., "Modified poly ($\epsilon$-caprolactone)s and their use for drug-encapsulating nanoparticles," Journal of Polymer Science Part A: Polymer chemistry, 2004, 42, 3 (pp. 689-700).
Johnston et al., "Networks from $\alpha,\omega$-Dihydroxypoly(dimethylsiloxane) and (Tridecafluoro-1,1,2,2-tetrahydrooctyl)triethoxysilane: Surface Microstructures and Surface Characterization," Macromolecules, vol. 32, No. 24, 1999 (pp. 8173-8182).
Karal et al., "Blend of polycaprolactone-poly (dimethylsiloxane)-polycaprolactone triblock copolymer with poly(vinyl chloride) preparation and characterization", Polymer, 1997, 38, 24 (pp. 6071-6078).
Kawakami et al., "Silicone Macromers for Graft Polymer Synthesis," Polymer Journal, vol. 14, No. 11, 1982 (pp. 913-917).
Kugel et al., "Synthesis, Characterization, and Antimicrobial Properties of Polysiloxane Coatings Containing Tethered Levofloxacin Moieties", presentation No. 628 at 235th ACS National Meeting, New Orleans, LA, (Apr. 10, 2008) 21 pages.
Kugel et al., "Synthesis, Characterization, and Antimicrobial Activity of Polysiloxane Coatings Containing Tethered Levofloxacin Moieties," Abstract for presentation at 235th ACS National Meeting, New Orleans, LA, (published Feb. 11, 2008), 4 pages.
Kugel et al., "Synthesis, Characterization, and Antimicrobial Activity of Polysiloxane Coatings Containing Tethered Levofloxacin Moieties," published in conjunction with the 235th ACS National Meeting, New Orleans, LA, (Apr. 2008), 2 pages.
Kugel et al., Antimicrobial Polysiloxane Polymers and Coatings Containing Pendant Levofloxacin, Polymer Chemistry, vol. 1, 442-452 (2010), 11 pages.
Lee et al., Journal of Applied Polymer Science, 2003, 87 (pp. 375-380).
Mahoney et al., Macromolecules, 2002, 35 (pp. 5256-5266).
Majumdar et al., "Influence of Solvent Composition and Degree of Reaction on the Formation of Surface Microtopography in a Thermoset Siloxane-Urethane System," *Polymer*, 47, 4172-4181 (2006).
Majumdar et al., "Preparation of Siloxane-Urethane Coatings Having Spontaneously Formed Stable Biphasic Microtopographical Surfaces," *Macromolecules*, 2005, vol. 38 (pp. 5857-5859).
Majumdar et al., "Thermoset Siloxane-Urethane Fouling Release Coatings," *A.C.S. Symposium Series*, 2007, vol. 957 (pp. 61-75).
Pieper et al., "Combinatorial approach to study the effect of acrylic polyol composition on the properties of crosslinked siloxane-polyurethane fouling-release coatings," *J. Coat. Technol. Res.*, 2007, 4(4) (pp. 453-461).
Smetankina et al., "Reactivity of organosilicon diisocyanates," XVII. Carcofunctional organosilicon compounds, Zhurnal Obshchei Khimii, 1974, 44(12) (pp. 2638-2641).

Stafslien et al., "Combinatorial materials research applied to the development of new surface coatings IV. A high-throughput bacterial biofilm retention and retraction assay for screening fouling-release performance of coatings," *Biofouling*, 2007, 23(1/2) (pp. 45-54).

Tang et al., "Anti-inflammatory properties of triblock siloxane copolymer-blended materials," Biomaterials, 1999, 20 (pp. 1365-1370).

Tezuka et al., "Environmentally induced Macromolecular Rearrangement on the Surface of Polyurethane-Polysiloxane Block Copolymers," J. Chem. Soc. Paraday Trans., vol. 87, 1991 (pp. 147-152).

Tezuka et al., "Environmentally Induced Macromolecular Rearrangement on the Surface of Polyurethane-Polysiloxane Graft Copolymers," Journal of Colloid and Interface Science, vol. 136, No. 2, May 1990 (pp. 408-414).

Thomas et al., "Silicones Containing Pendant Biocides for Antifouling Coatings," Biofouling, vol. 20, Nos. 4-5, Aug.-Oct. 2004 (pp. 227-236).

Yar et al., "Design of trageted dosage form of ofloxacin", *J. Serb. Chem. Soc.*, vol. 71, No. 12, 2006 (pp. 1269-1273).

Yilgor et al., "Novel triblock siloxane copolymer: Synthesis, characterization, and their use as surface modifying additives," Journal of Polymer Science Part A: Polymer chemistry, 1989, 27, 11, (pp. 3673-3690).

Zhuang et al., "Determination of the Distribution of Poly(dimethylsiloxane) Segment Lengths at the Surface of Poly[(dimethylsiloxane)-urethane]-Segmented Copolymers by Time-of-Flight Secondary Ion Mass Spectrometry", Macromolecules, vol. 30, No. 4, 1997 (pp. 1153-1157).

\* cited by examiner

SILOXANE POLYMER CONTAINING TETHERED FLUOROQUINOLONE

CROSS-REFERENCE TO RELATED APPLICATIONS

This patent application is a continuation of U.S. patent application Ser. No. 12/378,049, filed on Feb. 10, 2009, which claims the benefit of U.S. Provisional Patent Application 61/065,577, filed on Feb. 13, 2008, the entire contents of which are hereby incorporated by reference, for any and all purposes.

GOVERNMENT RIGHTS

The United States Government has rights in this invention pursuant to Contract No. N00014-06-1-0952 between the United States Government Office of Naval Research and North Dakota State University.

BACKGROUND

Medical devices in contact with, or implanted within, the human body can facilitate transmission of microbial pathogens into the body and cause infections in patients that are the recipients of such medical devices. When an infection occurs, it may result in serious health complications for the patient and require a variety of additional treatment regimens including antibiotics, and even the need for additional surgeries to remove the infected device and/or tissue surrounding the device.

Several strategies can be employed to help prevent microbial colonization and infection of medically implanted devices, including systemic administration of antibiotics and coating devices with antiseptic creams and gels. Another approach is to coat the devices with an antibiotic-impregnated coating which can extend the antimicrobial lifetime beyond that of antiseptic creams, and concentrate the activity directly at the site of implantation. The activity of such an antimicrobial coating is highly dependent on the sustained release of therapeutic levels of the antimicrobial agent. Several factors can influence the rate of release of these agents including the local environment (i.e., temperature, pH) and chemistry of the antimicrobial coating material itself (i.e., cross-link density, porosity, water permeability, etc.).

SUMMARY

The present application is directed to a functionalized polymeric material which includes one or more Levofloxacin groups. The Levofloxacin-functionalized polymeric material may be used to form antimicrobial coatings, e.g., for use in coating devices designed for medical applications. The polymeric material typically includes a polyorganosiloxane backbone, e.g., the polymeric material is a functionalized polydialkylsiloxane, which includes pendant Levofloxacin groups. The Levofloxacin groups are suitably attached to the polyorganosiloxane backbone by linker groups. It may also be desirable to include functional groups in the polyorganosiloxane which are capable of serving as sites for cross-linking reactions ("cross-linkable groups"). In some embodiments, the polymeric material may also include one or more texturizing moieties which may be introduced to alter and/or control the physical properties of the polymeric material. Examples of suitable texturizing moieties include hydrophilic groups, such as polyether groups, hydrophobic groups such as perfluoroalkyl groups, self-organizing groups, grafted polymers and/or copolymers such as grafted polymethacrylate including these functionalized ester groups, e.g., alkoxy alkyl ester groups. In many situations, compositions comprising the Levofloxacin-functionalized polymeric material, which are designed for use in coating applications, may also include other components, such as curing agents, crosslink initiators, and the like.

In one aspect, a polymer has the general formula

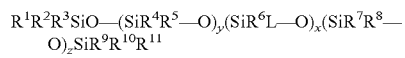

where $R^1$, $R^2$, $R^3$, $R^4$, $R^5$, $R^6$, $R^8$, $R^9$, $R^{10}$, and $R^{11}$ are independently $C_1$-$C_{20}$ alkyl, benzyl, tolyl, xylyl, or phenyl, $R^7$ is a $C_1$-$C_{20}$ alkyl, benzyl, tolyl, xylyl, phenyl, texturizing moiety, cross-linkable group, or a mixture of any two or more; L is a linker group, a linker group having a Levofloxacin group, or a mixture of any two or more; x is 1 to 100; y is 0 to 100; z is 0 to 100; at least one of y and z is greater than 0; and the polymer contains at least one Levofloxacin group. In some embodiments, the linker group is a $C_1$-$C_{20}$ alkylene group or a substituted $C_1$-$C_{20}$ alkylene group, optionally having one or more chain carbons substituted by a heteroatom (e.g., an oxygen, sulfur or nitrogen atom). In some embodiments, the weight average molecular weight of the polymer ranges from about 1,000 g/mol to about 65,000 g/mol. In other embodiments, the linker group—Levofloxacin group includes a hydrolytically labile linkage. In some embodiments, the hydrolytically labile linkage is an ester or an anhydride linkage. In other embodiments, the hydrolytically labile linkage includes an ether. In yet other embodiments, the linker group is a $C_3$-$C_{20}$ group having at least one ether and at least one alcohol.

In some embodiments, the polysiloxane polymer includes, but is not limited to, poly(methylhydro-co-dimethyl)siloxane, polymethylhydrosiloxane, polydimethylsiloxane, polyethylhydrosiloxane, polyphenyl-(dimethylhydro)siloxane, methylhydrosiloxane-phenylmethylsiloxane copolymer, and methylhydrosiloxane-octylmethylsiloxane copolymer. In other embodiments, the polysiloxane polymer is a functionalized polydialkylsiloxane. Suitable cross-linkable groups, include, but are not limited to pendent hydroxyl groups, carboxylic acid groups, amine epoxy groups, pendent anhydride groups, or a mixture of any two or more In another aspect, a method of preparing a Levofloxacin-functional polysiloxane is provided. Such methods include reacting a polysiloxane polymer with Levofloxacin or a pharmaceutically acceptable salt Levofloxacin to form a polysiloxane polymer having grafted Levofloxacin groups.

In another aspect, a method of releasing Levofloxacin groups from a Levofloxacin-functional polysiloxane is provided. Such methods include contacting a Levofloxacin-functional polysiloxane with an aqueous medium, wherein, the Levofloxacin-functional polysiloxane includes a polysiloxane, Levofloxacin groups, and wherein the Levofloxacin groups are connected to the polysiloxane via a linker. In such embodiments, the linkers contain a hydrolytically labile linkage. Such hydrolytically labile linkages include, but are not limited to ester or anhydride linkage.

In another aspect, coating compositions having the above polysiloxanes are described. The polysiloxane may also include a multifunctional amine cross-linker to be used upon clearing.

In yet another aspect, a substrate coated with a cured polymer includes the substrate, the Levofloxacin-polysiloxanes described herein, and a multifunctional amine cross-linker, wherein the polymer and the cross-linker are cured.

In another aspect, a method of preparing a Levofloxacin-functional polysiloxane is provided, including, reacting a polysiloxane polymer with Levofloxacin, or a pharmaceutically acceptable salt of Levofloxacin, to form a polysiloxane polymer having grafted Levofloxacin groups. In some embodiments, the method also includes reacting the polysiloxane polymer with an allyl epoxy ether to form a polysiloxane polymer having pendent epoxy groups. In some such embodiments, the allyl epoxy ether is allyl glycidyl ether. In other embodiments, the method also includes reacting the polysiloxane polymer with an anhydride to form an anhydride-functional polysiloxane. In some such embodiments, the anhydride is norbornene anhydride.

In another aspect, a method of releasing Levofloxacin groups from a Levofloxacin-functional polysiloxane includes contacting a Levofloxacin-functional polysiloxane with an aqueous medium; wherein, the Levofloxacin-functional polysiloxane includes: a polysiloxane; Levofloxacin groups; and linkers wherein the Levofloxacin groups are connected to the polysiloxane via the linkers.

DETAILED DESCRIPTION

Definitions

Figure 1:
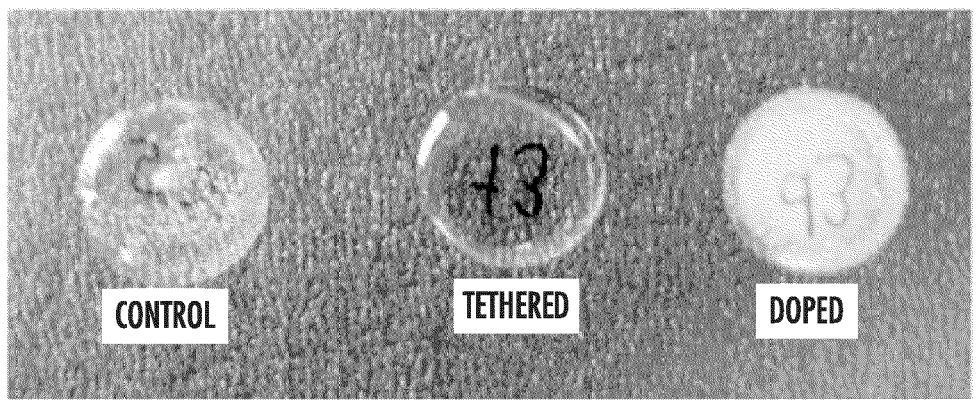
FIG. 1 is a photograph of side-by-side sample of coatings on glass cover slips, after curing, of a tethered Levofloxacin-polysiloxane polymer (tethered), a control polymer (control), and a doped polymer (doped).

As used herein, the term "alkyl" includes straight chain and branched alkyl groups having from 1 to about 20 carbon atoms, and typically from 1 to 12 carbons or, in some embodiments, from 1 to 10 carbon atoms. Alkyl groups further include cycloalkyl groups. Examples of straight chain alkyl groups include those with from 1 to 10 carbon atoms such as methyl, ethyl, n-propyl, n-butyl, n-pentyl, n-hexyl, n-heptyl, n-octyl, n-nonyl, n-decyl groups, and the like. Examples of branched alkyl groups include, but are not limited to, isopropyl, iso-butyl, sec-butyl, tert-butyl, neopentyl, isopentyl, 2,2-dimethylpropyl groups, and the like. Representative substituted alkyl groups may be substituted one or more times with substituents.

In general, "substituted" refers to an organic group, such as an alkyl group, in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. Substituted cycloalkyl groups may also include epoxy groups. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

For the purposes of this disclosure and unless otherwise specified, "a" or "an" means "one or more."

The word "or" when used without a preceding "either" (or other similar language indicating that "or" is unequivocally meant to be exclusive—e.g., only one of x or y, etc.) shall be interpreted to be inclusive, that is "or" when it appears alone shall mean both "and" and "or." Likewise, as used herein, the term "and/or" shall also be interpreted to be inclusive in that the term shall mean both "and" and "or." In situations where "and/or" or "or" are used as a conjunction for a group of three or more items, the group should be interpreted to include one item alone, all of the items together, or any combination or number of the items.

Terms used in the specification and claims such as have, having, include, and including should be construed to be synonymous with the terms comprise and comprising.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "texturizing group" refers to groups that enhance the textural properties of the copolymer and/or the final product which incorporates the copolymer. Such texturizing groups include, but are not limited to hydrophilic groups such as polyether groups, hydrophobic groups such as perfluoroalkyl groups, liquid crystalline groups such as deuterobenzene groups, self-organizing groups, polymers and copolymers such as polymethacrylate including these groups, etc., or a texturizing moiety (e.g., alkoxy alkyl groups such as alkoxy alkyl functional polymethacrylate (either polymer or copolymer), etc.

DESCRIPTION

In one aspect, siloxane polymers containing tethered antibacterial agents, such as Levofloxacin, which provide antimicrobial activity, are described. Such siloxane polymers may be used to coat a variety of medical devices including, but not limited to, artificial joints, heart valves, tracheal tubes, vascular stints, venous catheters, urethral catheters, dental devices, prosthetic limbs, and the like.

Levofloxacin is an advanced, broad spectrum fluoroquinolone antibiotic with strong activity against a variety of pathogenic gram negative and gram positive bacteria. It is the S-enantiomer (i.e. the L-isomer) of ofloxacin. The IUPAC name for Levofloxacin is (−)-(S)-9-fluoro-2,3-dihydro-3-methyl-10-(4-methyl-1-piperazinyl)-7-oxo-7H-pyrido[1,2,3-de]-1,4-benzoxazine-6-carboxylic acid, and it has the following structure:

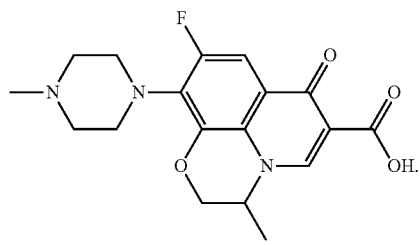

Generally, the antimicrobial siloxane polymers may be described as a siloxane polymer having pendant antibiotic groups. Such materials may be prepared via reaction of a polysiloxane and a linker, where the linker will eventually form the tether linking the antibiotic to the polysiloxane. To facilitate the reaction, the polysiloxane has residual Si—H groups, or other reactive sites, and a linker group that has reactive groups at each end.

The reactive groups at each end of the linker are different such that a first reactive group of the linker group will react with the polysiloxane and a second reactive group will remain available for further functionalization. In some embodiments, the first reactive group will react with the Si—H groups, or other reactive groups of the polysiloxane. For example, such first reactive groups include olefins such as allyl and other vinylic groups. In some embodiments, the second reactive is a group that will react with groups on other moieties, such as an antibiotic moiety, to result in the other moieties being pendent from the polysiloxane. For example, the second reactive group may be a group such as an epoxy group or an anhydride group. The linker group may be a $C_3$-$C_{20}$ group. Such groups may have allyl and epoxy groups such as, but not limited to, allyl epoxy ethers, such as allyl glycidyl ether, or the linker group may be a group having an anhydride moiety such as, but not limited to, a norbornene anhydride. For example, some specific linkers include 7-(allyloxy)-4-methyl-2H-chromen-2-one, 3-vinyl-7-oxabicyclo[4.1.0]heptane, bicyclo[2.2.1]hept-5-ene-2-carbaldehyde, 3-(2-methyl-prop-1-enyl)dihydrofuran-2,5-dione, and cis-5-norbornene-endo-2,3-dicarboxylic anhydride as illustrated below.

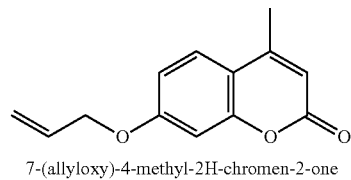

7-(allyloxy)-4-methyl-2H-chromen-2-one

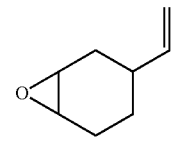

3-vinyl-7-oxabicyclo-
[4.1.0]heptane

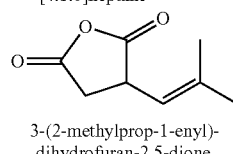

3-(2-methylprop-1-enyl)-
dihydrofuran-2,5-dione

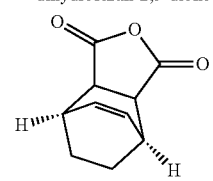

cis-5-norbornene-endo-
2,3-dicarboxylic anhydride

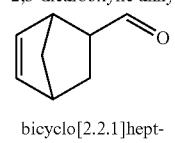

bicyclo[2.2.1]hept-
5-ene-2-carbaldehyde

Siloxanes to which the antibiotics may be attached have the general formula $R^1R^2R^3SiO$-$(SiR^4R^5—O)_y(SiR^6H—O)_x(SiR^7R^8—O)_zSiR^9R^{10}R^{11}$; where $R^1$, $R^2$, $R^3$, $R^4$, $R^5$, $R^6$, $R^8$, $R^9$, $R^{10}$, and $R^{11}$ are independently $C_1$-$C_{20}$ alkyl, benzyl, tolyl, xylyl, or phenyl; $R^7$ is a $C_1$-$C_{20}$ alkyl, benzyl, tolyl, xylyl, phenyl, a texturizing moiety, a cross-linkable group, or a mixture of any two or more; x is 1 to 100; y is 0 to 100; z is 0 to 100; and at least one of y and z is greater than 0. The polysiloxane typically has from about 5% to about 75% Si—H groups in the polysiloxane.

In one embodiment, the polysiloxane is poly(methylhydroco-dimethyl)siloxane, polymethylhydrosiloxane, polydimethylsiloxane, polyethylhydrosiloxane, polyphenyl-(dimethylhydro) siloxane, methylhydrosiloxane-phenylmethylsiloxane copolymer, or methylhydrosiloxane-octylmethylsiloxane copolymer. In one embodiment, the weight average molecular weight of the polysiloxane ranges from about 500 g/mol to about 65,000 g/mol. In some embodiments, the weight average molecular weight of the polysiloxane is from about 500 g/mol to about 15,000 g/mol. Other polysiloxanes having the appropriate functionality will be readily recognized by those of skill in the art.

In the embodiment shown previously, the polysiloxane backbone may be a random or block copolymer. Accordingly, the formulas shown herein should be understood to refer to either a block or random copolymer having the specified monomeric units in any order.

In one embodiment, the antibiotic is Levofloxacin. In such embodiments, the Levofloxacin is pendent from the polysiloxane via a linkage, or tether. The linkage may be a substituted or unsubstituted $C_3$-$C_{20}$ linkage, or a substituted or unsubstituted anhydride linkage. Such pendent groups are said to be grafted to the polysiloxane.

The amount of Levofloxacin present on the polymer may vary by application. In some embodiments, the Levofloxacin groups are present from about 0.1 wt % to about 50 wt %, from about 1 wt % to about 40 wt %, from about 5 wt % to about 30 wt %, from about 5 wt % to about 20 wt %, or from about 5 wt % to about 15 wt %. In some case, the Levofloxacin will account for about 5 wt % to about 10 wt %. Such weight percentages are based upon the weight of the Levofloxacin and the total weight of the polymeric materials.

The Levofloxacin-functional polysiloxanes may have the following general structure: $R^1R^2R^3SiO$-$(SiR^4R^5$—$O)_y$-$(SiR^6L$—$O)_x(SiR^7R^8$—$O)_zSiR^9R^{10}R^{11}$; where $R^1$, $R^2$, $R^3$, $R^4$, $R^5$, $R^6$, $R^8$, $R^9$, $R^{10}$, and $R^{11}$ are independently $C_1$-$C_{20}$ alkyl, benzyl, tolyl, xylyl, or phenyl; $R^7$ is a $C_1$-$C_{20}$ alkyl, benzyl, tolyl, xylyl, phenyl, a texturizing group, a cross-linkable group, or a mixture of any two or more; L is independently a linker group, a linker group with a Levofloxacin group, or a mixture of any two or more; x is 1 to 100; y is 0 to 100; z is 0 to 100; at least one of y and z is greater than 0; and the polymer contains at least one Levofloxacin group. Linker groups include $C_1$-$C_{20}$ alkyl groups and substituted $C_1$-$C_{20}$ alkyl groups. The weight average molecular weight of the polymer may range from about 500 g/mol to about 65,000 g/mol, in some embodiments.

In other embodiments, the linkage is a hydrolytically labile linkage. "Hydrolytically labile" is used to refer to a group that is readily susceptible to scission in aqueous media to release the group that is pendent. For example, in the case of a polysiloxane having Levofloxacin groups pendent from the polysiloxane via a $C_3$-$C_{20}$ linkage, under aqueous conditions the linkage is cleaved to release the Levofloxacin. A variety of pH conditions may also be used. For example, the pH may be less than about 8. For example, some aqueous solutions may be buffered with phosphate buffer solution at a pH of from about 7 to 7.5. Examples of hydrolytically labile linkages include, but are not limited to, ester and anhydride linkages or moieties.

The general structure thus described, Schemes I and II describe the synthetic process used to produce a polysiloxane having pendent Levofloxacin groups, according to one embodiment.

Scheme III:

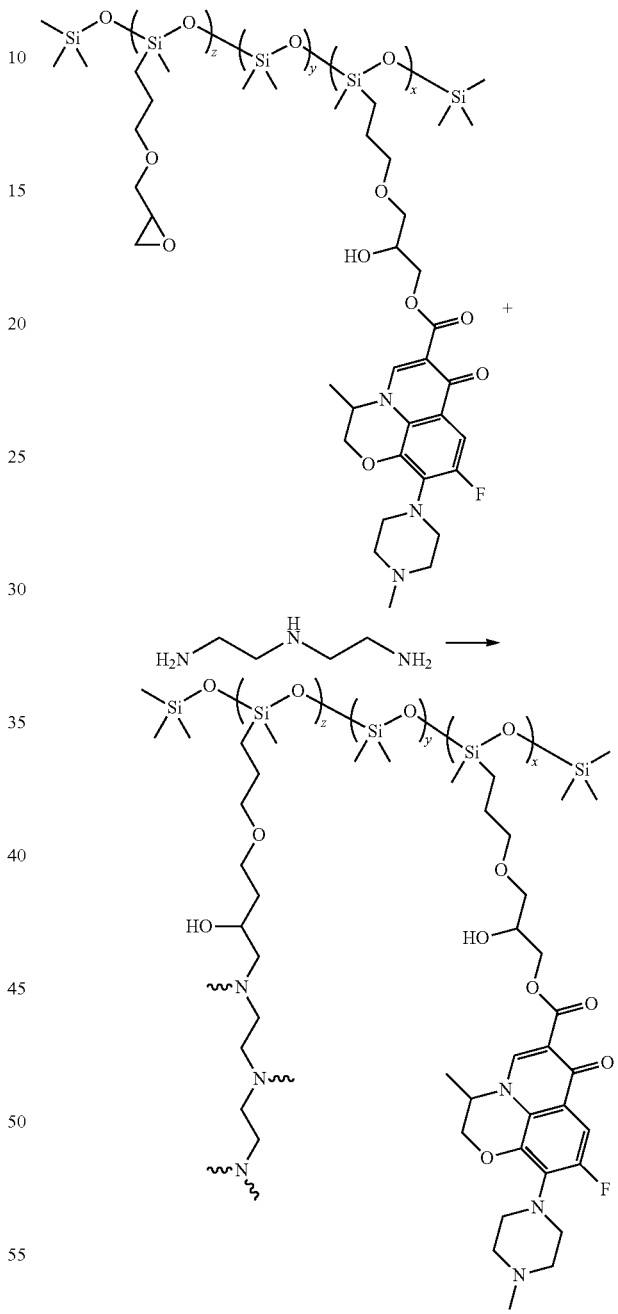

Scheme I:

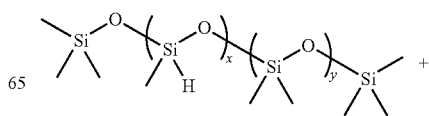

-continued

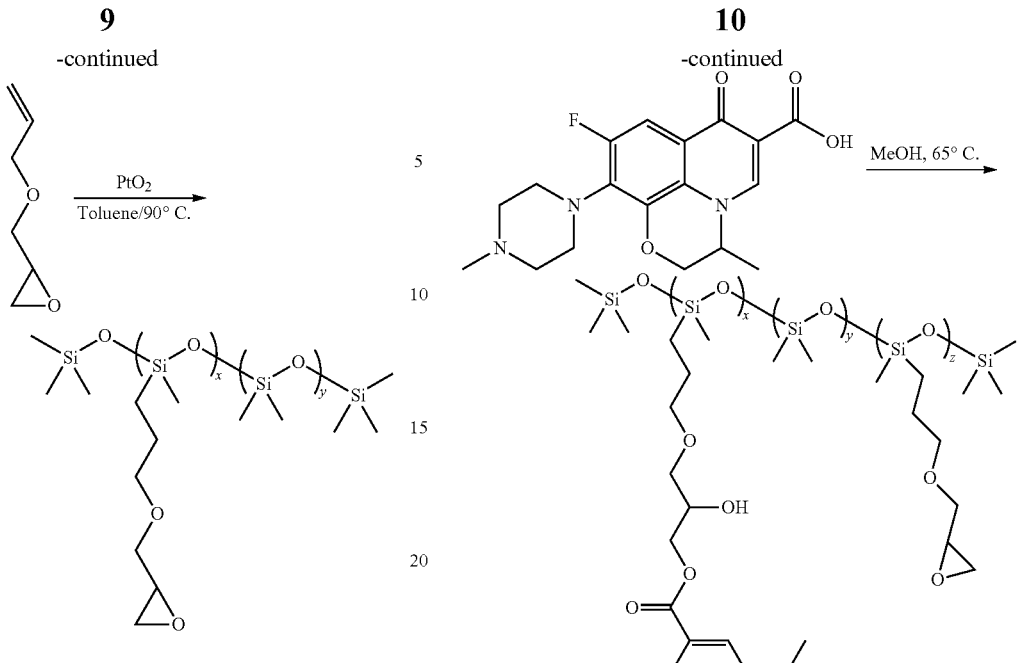

According to such embodiments, as shown above in Schemes I and II, the synthesis may be a two-step process in which glycidyl ether groups are grafted to a polysiloxane copolymer, via hydrosilylation chemistry, and then a portion of the epoxides are subsequently reacted with Levofloxacin, or a pharmaceutically acceptable salt thereof, to produce an ester-functional tether, or linker group, joining the Levofloxacin to the polysiloxane backbone. Pharmaceutically acceptable salts of Levofloxacin include, but are not limited to, salts prepared by reaction of the carboxylic acid of Levofloxacin with a base. For example the base may be an alkali metal base, an alkaline earth base, or an ammonium base as are known to those of skill in the art including, but not limited to lithium, sodium, or potassium hydroxide and alkoxides; lithium, sodium, potassium, calcium, or magnesium carbonates; and the like.

While specific temperatures are disclosed in Schemes I and II, these temperatures are not limiting. For example, in Scheme I, temperatures may vary from about 50° C. to 150° C., in some embodiments, from about 60° C. to 125° C., in other embodiments, and from about 70° C. to 110° C., in yet other embodiments.

Scheme II:

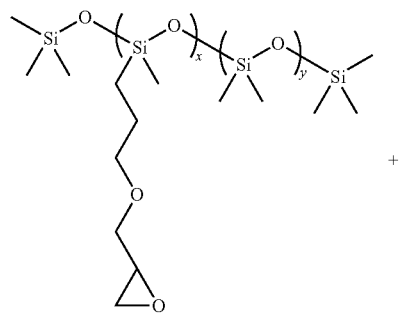

As shown in Scheme III, a Levofloxacin-functionalized polysiloxane, such as the one shown in Scheme II, may be crosslinked with an appropriate cross-linking agent to form a cured coating.

The synthesis of the reactive polysiloxane containing tethered Levofloxacin groups via an anhydride linkage is illustrated as a two step process. The two step process involves first grafting the anhydride groups to the polysiloxane copolymer using hydrosilylation chemistry. Second, the grafted anhydride groups are reacted with Levofloxacin to produce the Levofloxacin-functional tether. This is illustrated in Scheme IV. Cross-linked coatings may then be prepared from the copolymer using the carboxylic acid groups. For example, a multi-isocyanate-functional compound could be used to cross-link the copolymer by reaction of isocyanate groups of the cross-linker with carboxylic acid groups of the copolymer to produce amide cross-links.

Scheme IV:

Step 1: Synthesis of anhydride functional siloxane

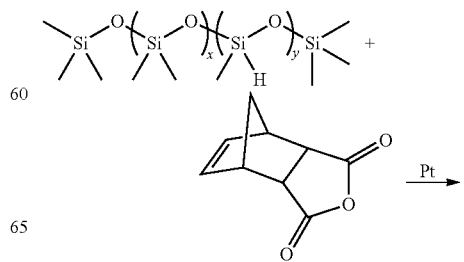

-continued

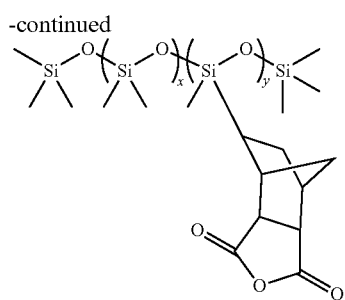

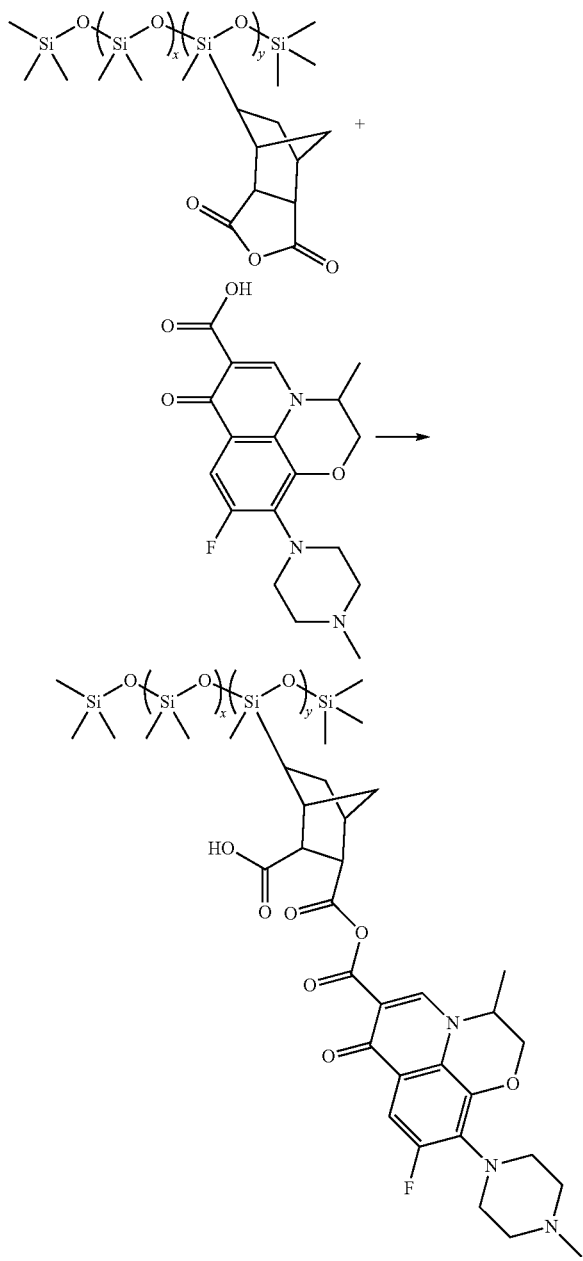

Step 2: Functionalization with Levofloxacin

In yet another aspect, coatings of the polysiloxanes having pendent antibiotic groups may be prepared via solution blending of the antibiotic-grafted polysiloxanes with a multifunctional amine cross-linker. The mixture is then allowed to cure at a slightly elevated temperature until the polymer is cured. The temperature is elevated to ensure a complete cure, although only relatively low temperatures are required. For example, in some embodiments, the temperature is from about 30° C. to about 100° C., from about 40° C. to about 75° C., or from about 45° C. to about 55° C.

The multifunctional amine cross-linker may be selected from any of a number of compounds known to those of skill in the art. Such multifunctional amine cross-linkers may include, but are not limited to, diethylenetriamine, 1,4-diaminobutane; bis(dimethylamino)-dimethylsilane; 1,3-dipyridyl propane; 1,3-bis(N,N-dimethylamino)-butane; 1,n-bis(N,N-dialkylamino)-alkane where N,N-dialkyl groups are ethyl and/or methyl and 1,n-substituted alkane backbone typically has from 2 to 10 carbon atoms, bis(aminoalkyl)-benzene such as 1,4-bis(N,N-dimethylaminomethyl)-benzene or 1,3-di-(aminoethyl)-benzene; 1,n-bis(N,N-dialkylamino)-cycloalkane such as 1,4-bis(N,N-dimethylamino)-cyclohexane or 1,4-bis(N,N-dimethylaminomethyl)-cyclohexane; 1,n-dipyridyl alkane such as 1,3-dipyridyl butane or 1,6-dipyridyl hexane; 1,n-dipyridyl cycloalkane such as 1,4-dipyridyl cyclohexane; polyalkylenepolyamine such as N,N,N',N'',N''-pentamethyldiethylenetriamine, tetraethylenetriamine, or N,N,N',N'-tetramethylpropylenediamine; N,N,N',N'-tetramethyl-1,4-butanediamine; N,N,N'N'-tetramethyl-ethylenediamine; N,N,N'N'-tetramethyl-1,6-hexanediamine; N,N,N'N'-tetramethylbenzidine; N,N,N',N'-tetraethylethylenediamine; 2,2'-dipyridyl; and 4,4'-dipyridyl. Other cross-linkers include materials such as EPI-CURE 3292-FX-60, EPI-CURE 3370, EPI-CURE 3200, EPI-CURE 3213, EPI-CURE 3300, EPI-CURE 3175, EPI-CURE 3010, EPI-CURE 3090, EPI-CURE 3251, EPI-CURE 3164, EPI-CURE 3140, and EPI-CURE 3270 all of which are available from Hexion Chemicals.

The present invention, thus generally described, will be understood more readily by reference to the following examples, which are provided by way of illustration and are not intended to be limiting of the present invention.

EXAMPLES

The raw materials used for the examples are described in the table below:

| Raw Material | Description | Manufacturer |
| --- | --- | --- |
| HMS-501 | Poly(methylhydro-co-dimethyl)-siloxane | Gelest |
| Allyl glycidyl ether | Ally 2,3-epoxypropyl ether | Aldrich |
| Platinum oxide | Powder | Aldrich |
| Levofloxacin | (−)-(S)-9-fluoro-2,3-dihydro-3-methyl-10-(4-methyl-1-piperazinyl)-7-oxo-7H-pyrido-[1,2,3-de]-1,4-benzoxazine-6-carboxylic acid | Fluka |
| Norbornene anhydride | cis-5-Norbornene-endo-2,3-dicarboxylic anhydride | Aldrich |
| Diethylenetriamine | N-(2-aminoethyl)-1,2-ethanediamine | Aldrich |

Example 1

Synthesis of glycidyl ether functional polysiloxane (epoxy-PDMS). Allyl glycidyl ether (13.2 mL, 0.111 mol) was added to HMS-501 (10.0 g, 0.0741 mol) in toluene. A catalytic amount of $PtO_2$ was added, and the mixture was heated at 90° C., overnight. An NMR spectrum taken the following day showed there to be substantially no remaining hydride (peak at approx. 4.7 ppm). The reaction mixture was then cooled and passed through a bed of aluminum oxide layered on top of a fitted glass filter. The frit was washed with additional toluene. The eluent was collected in a round-bottom flask. The solvent and residual allyl glycidyl ether were then removed in vacuo at 50° C., to yield the epoxy-PDMS as a thick clear liquid (16.09 g, 87.2%).

Example 1A

Alternative Synthetic Procedure: Synthesis of glycidyl ether functional polysiloxane (epoxy-PDMS). Allyl glycidyl ether (17.5 mL, 0.148 mol) was added to HMS-501 (20.0 g, 0.148 mol) in toluene (50 g). A catalytic amount of platinum-divinyltetramethylsiloxane in xylene (30 µL, Pt~2%), and the mixture was heated in a Radley® Reactor system equipped with a nitrogen blanket and temperature controller set at 80° C. The reaction was monitored via proton NMR, and allyl glycidyl ether was added periodically until the Si—H resonance at 4.8 ppm disappeared in the NMR spectrum. The toluene and excess allyl glycidyl ether (if present) were removed in vacuo to yield the epoxy-PDMS as a thick clear liquid.

Example 2

Synthesis of a Levofloxacin-functional polysiloxane. Epoxy-PDMS from Example 1 (0.50 g) and Levofloxacin (0.75 g) were dissolved in methanol (35 mL) and the resultant reaction mixture was heated at reflux (18 hr). The methanol was removed under reduced pressure to yield Levo-epoxy-PDMS as a homogeneous, viscous yellow liquid. The product was characterized using nuclear magnetic resonance (NMR) spectroscopy. The Levo-epoxy-PDMS contained 13 wt % Levofloxacin.

Example 2A

Alternative Synthetic Procedure: Epoxy-PDMS from Example 1A (3.6 g, 0.015 eq.) and Levofloxacin (0.18 g, 0.00054 eq.) were dissolved in methanol (4.24 g) and the resultant reaction mixture was heated at 65° C. for 2.5 hr. The methanol was removed under reduced pressure to yield Levo-epoxy-PDMS as a homogeneous, viscous yellow liquid. The product was characterized using nuclear magnetic resonance (NMR) spectroscopy. The Levo-epoxy-PDMS contained 5 wt % Levofloxacin.

Example 3

Cross-linked coating containing tethered Levofloxacin moieties. The polymer from Example 2 was cured into a coating using diethylenetriamine (DETA) as a cross-linking agent. Levo-epoxy-PDMS (1.0 g) from Example 2 was dissolved in methanol (1.0 mL) and DETA (0.025 g) was added to the solution. The solution was thoroughly mixed and coated on to glass cover slips by depositing approximately 3-4 drops of the solution per cover slip. Curing of the Levo-epoxy-PDMS on the cover slips was accomplished at 50° C., overnight. The cured Levo-epoxy-PDMS drops contained 13 wt % Levofloxacin.

Example 4

Synthesis of a anhydride-functional polysiloxane (anhydride-PDMS). Norbornene anhydride (1.22 g) was reacted with HMS-501 (1.0 g) in toluene (20 g) at 90° C., in the presence of platinum oxide as a catalyst. The reaction progress was monitored by $^1$H NMR. Upon reaction completion, the catalyst was removed by filtration and the solvent was removed under reduced pressure to yield the anhydride-PDMS as a highly viscous liquid.

Example 5

Synthesis of a Levofloxacin-functional polysiloxane from anhydride-PDMS. The anhydride-PDMS (0.2781 g), from Example 4, and Levofloxacin (0.336 g) were refluxed at 70° C. in chloroform (15 g). The reaction was monitored by $^1$H NMR and $^{13}$C NMR. Upon completion, the product was collected under reduced pressure.

Example 6

Synthesis of anhydride-functional polysiloxane. Cis-5-norbornene-endo-2,3-dicarboxylic anhydride (0.0254 g), HMS-501 (1.4741 g), toluene (6.9 g), and catalytic platinum oxide were added to a flask and heated at 90° C., with stirring. The reaction was monitored using $^1$H NMR. Remaining Si—H groups were then reacted with excess allyltrimethyl silane, which was added directly to the reaction mixture. The allyl trimethyl silane reaction was also monitored by $^1$H NMR. Upon disappearance of the Si—H peak (4.8 ppm), the solvent and unreacted allyltrimethylsilane were removed under reduced pressure to yield the anhydride-functional polysiloxane.

Example 7

Synthesis of a Levofloxacin-functional polysiloxane from anhydride-PDMS. The anhydride-functional polysiloxane of Example 6 (1.47 g) was charged to a flask with Levofloxacin (0.07 g) and chloroform (5 mL). The mixture was heated at 60° C. for 72 hr under magnetic stirring. The reaction mixture was added to toluene (50 mL) and washed three times with an equal amount of water to remove unreacted Levofloxacin. The product was collected by solvent removal under reduced pressure. Using UV light at 365 nm, the presence of Levofloxacin on the anhydride-PDMS polymer was confirmed versus the non-absorbing anhydride-PDMS (Example 6).

Reference 1: Cross-linked control coating not containing Levofloxacin moieties. The epoxy-PDMS (1.0 g) from Example 1 was dissolved in methanol (1.5 mL) and DETA (0.085 g) was added. The solution was thoroughly mixed and coated onto glass cover slips by depositing approximately 3-4 drops of solution per cover slip. Curing of the epoxy-PDMS on the cover slip was accomplished at 50° C., overnight.

Reference 2: Cross-linked coating containing Levofloxacin as an additive (non-tethered or doped). Epoxy-PDMS (1.0 g) from Example 1 and Levofloxacin (0.15 g) were dissolved in chloroform (1.0 mL), and DETA (0.085 g) added. The solution was thoroughly mixed and coated onto glass cover slips by depositing approximately 3-4 drops of the solution per cover slip. Curing was accomplished at 50° C., overnight.

FIG. 1 displays photographs of Example 3 (Tethered), Reference 1 (Control), and Reference 2 (Doped). From the figure, it can be clearly seen that Reference 2 is hazy. Without being bound by theory, the hazy appearance is thought to be due to crystallization of the Levofloxacin within the coating. The coating solution was completely soluble; however, upon solvent evaporation, crystallization of the Levofloxacin took place indicating poor solubility of the Levofloxacin in the polysiloxane matrix. Unlike Reference 2, Example 3 (Tethered) remained transparent upon curing of the polymer. This result in consistent with Levofloxacin being tethered to the polysiloxane matrix resulting in a homogeneous, one-phase coating.

Coated glass cover slips of Example 3, Reference 1, and Reference 2 were individually placed in 20 ml scintillation vials and 10 ml of sterile phosphate buffered saline (PBS, pH is 7.3-7.5) was added. The scintillation vials were then placed in a dark cabinet, under ambient conditions (~25° C.), with no agitation. At each sampling period (1, 3 and 7 days), the entire volume of PBS-polymer leachate was removed and 10 ml of fresh PBS was added. The PBS-polymer leachates collected were used for determination of the quantity of Levofloxacin released and any antibacterial activity.

The concentration of Levofloxacin in each PBS-polymer leachate was determined using an Agilent 1100 series HPLC. The mobile phase consisted of 83% triethylamine (TEA) in nanopure $H_2O$ (40% TEA in water, pH 3.0) and 17% acetonitrile. A Zorbax Eclipse XDB-C18 reverse phase column (4.6×150 mm, 5 μm) was used for chromatographic separation at a flow rate of 1.2 ml/min, 6 minute runtime, injection volume of 0.020 ml, and column temperature of 20C. A diode array detector was used for UV absorbance measurements of Levofloxacin at 299 nm. Levofloxacin had a retention time of 2.8 minutes and was quantified using peak area calibrated against a standard curve. The limit of detection was determined to be 500 ng/ml. Table 1 shows the total amount of Levofloxacin released as determined by HPLC. From the table, it can be seen that Example 3 releases a significantly higher concentration of Levofloxacin at all sampling times, than the References.

TABLE 1

| Specimen | Sampling Time | Levofloxacin (ng/mL) |
|---|---|---|
| Reference 1 | 1 day | <500 |
| Reference 2 | 1 day | <500 |
| Example 3 | 1 day | 5933 |
| Reference 1 | 3 days | <500 |
| Reference 2 | 3 days | <500 |
| Example 3 | 3 days | 12853 |
| Reference 1 | 7 days | <500 |
| Reference 2 | 7 days | <500 |
| Example 3 | 7 days | 4225 |

Figure 2:
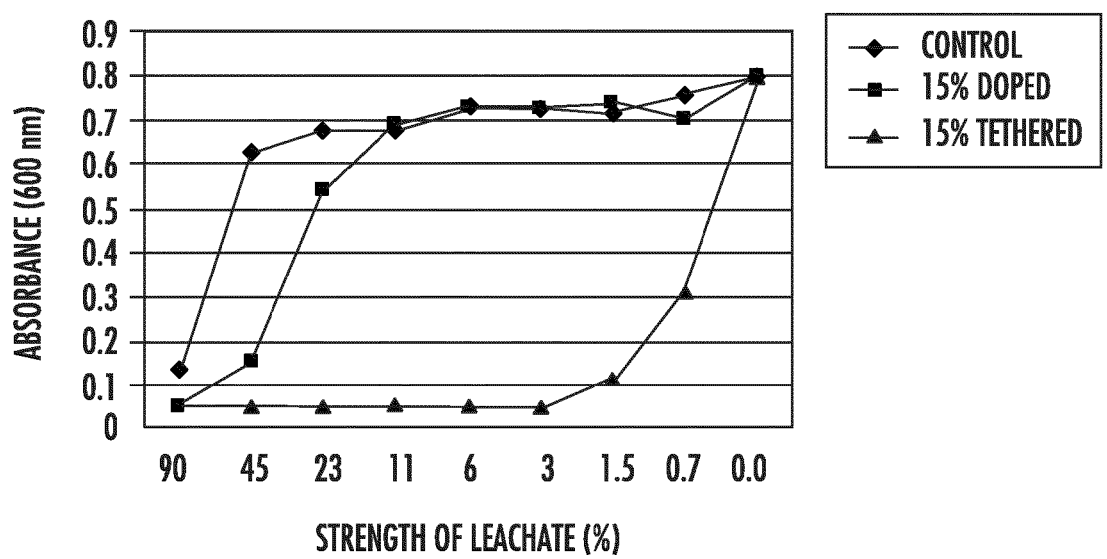
FIG. 2 is a graph illustrating the release profile of Levofloxacin from a polysiloxane polymer after 1 day in PBS solution.
Figure 3:
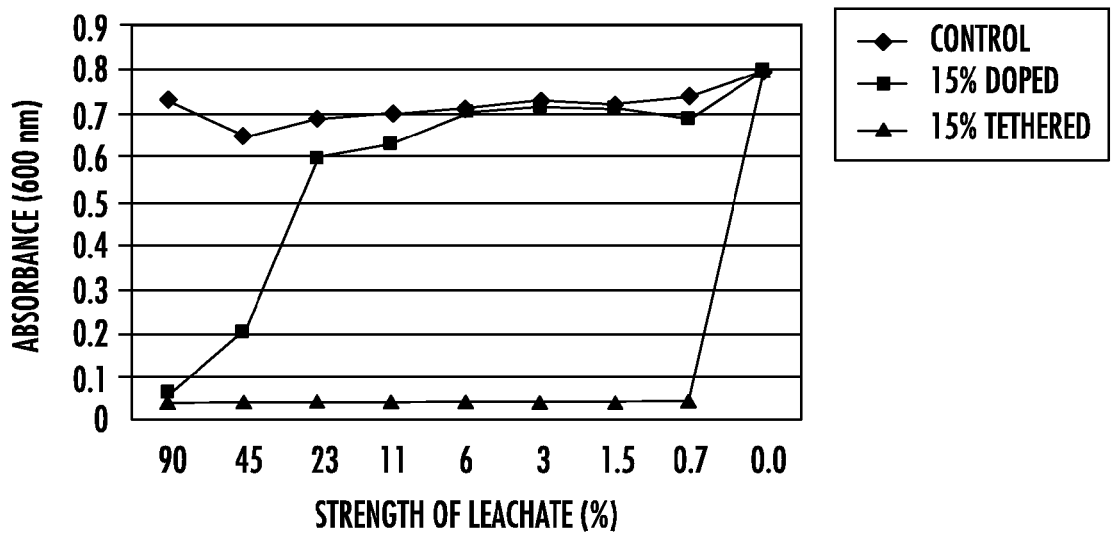
FIG. 3 is a graph illustrating the release profile of Levofloxacin from a polysiloxane polymer after 3 days in PBS solution.
Figure 4:
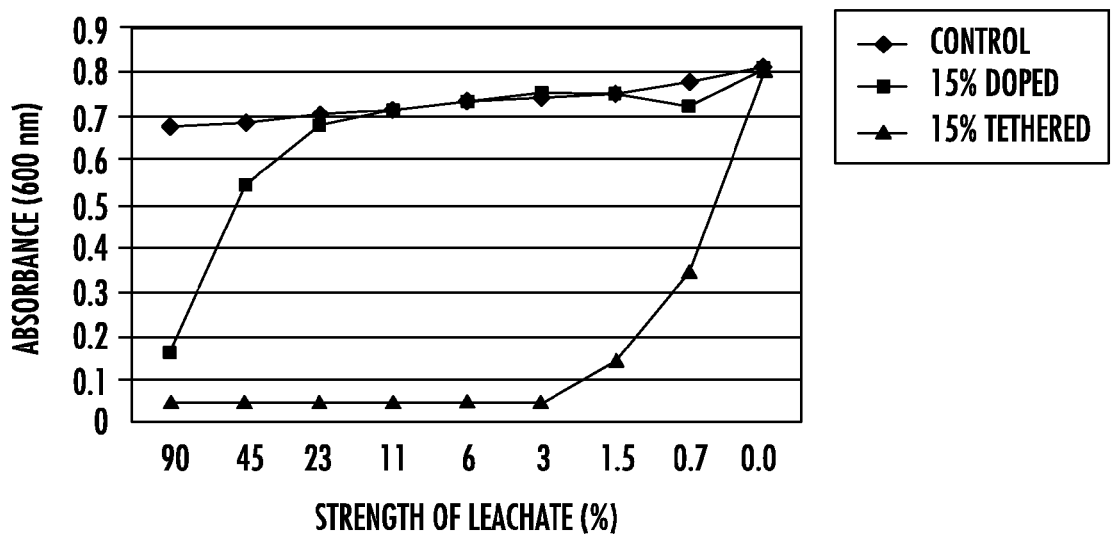
FIG. 4 is a graph illustrating the release profile of Levofloxacin from a polysiloxane polymer after 7 days in PBS solution.

For the evaluation of antimicrobial activity, 10×LB broth (0.1 mL) was added to each of the PBS-polymer leachates (0.9 mL), and the resulting solution was serially diluted 1:2 with 1×LB broth. An overnight culture of the bacterium *Escherichia coli* in LB broth was pelleted via centrifugation and re-suspended in PBS. A 1:80 dilution of the *E. coli* re-suspension in PBS (0.02 mL) was used to inoculate each PBS-polymer leachate dilution. Each of the dilutions (0.15 mL) was transferred in triplicate to a 96-well plate and placed in a 37° C. incubator overnight without shaking Turbidity measurements were made at 600 nm to determine the amount of *E. coli* growth is solution. The FIGS. 1-3 show the growth of *E. coli* in each PBS-polymer leachate as determined by turbidity measurements at 600 nm. From the figures, it can be seen that the leachates from Example 3 (15% tethered) were much more lethal to *E. coli* than either Reference 1 (Control) or Reference 2 (15% Doped).

Antimicrobial activity of the coatings before and after conditioning by water immersion was characterized by placing inverted coated glass cover slips on a Lauria-Bertani (LB) agar plate inoculated with ~$10^7$ cells/ml of the Gram-negative bacterium, *Escherichia coli*. A respiratory dye, 2,3,5-triphenyltetrazolium chloride (TTC), was incorporated into the LB agar (70 mg/l) to visualize the bacterial growth (red color). Agar plates with inverted coating discs were incubated for 48 hours at 37° C. and examined for both zones of growth inhibition and inhibition of growth on the coating surfaces.

Figure 5:
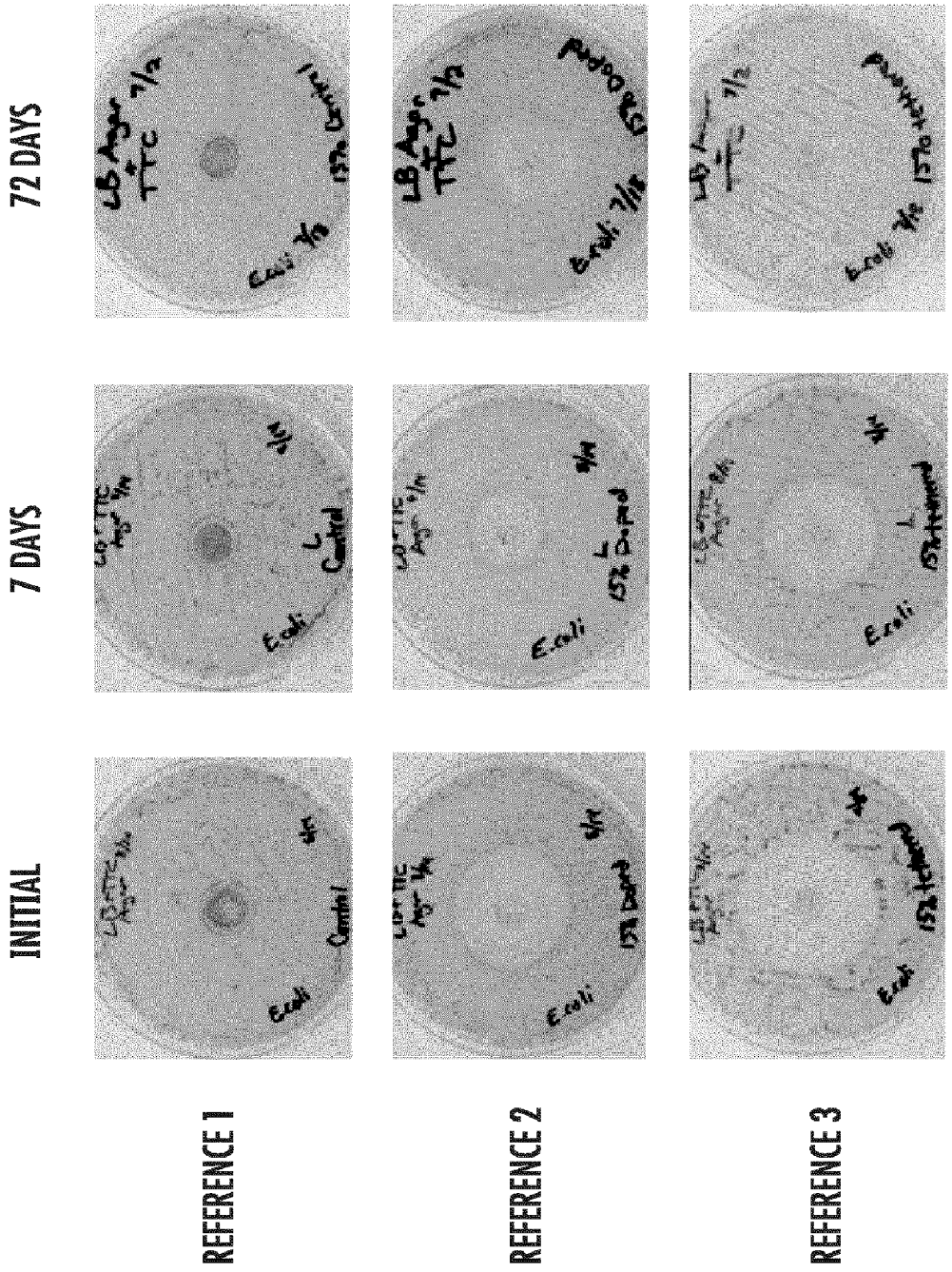
FIG. 5 is a photograph of glass cover slips coated with various Levofloxacin preparations, in agar plates inoculated with *Escherichia coli*, taken initially, at seven days, and at seventy two days.

As shown in FIG. 5, Reference 1 showed extensive microbial growth on the surface of the coating and no evidence of a zone of inhibition. In contrast, both Reference 2 and Example 3 showed antimicrobial activity on the surface of the coating and a relatively large zone of inhibition for the samples that were not immersed in water ("initial" in FIG. 5). Interestingly, for the "initial" specimens, the zone of inhibition for Example 3 was much larger than that for Reference 2, thereby indicating greater Levofloxacin release from the tethered sample.

After 72 days of immersion in water, Reference 2 displayed antimicrobial activity on the coating surface and a zone of inhibition, while Example 3 showed antimicrobial activity at the coating surface. This result suggests that the zone of inhibition observed for the tethered sample before water immersion was most likely due to leaching of residual, unreacted Levofloxacin from the coating. After sufficient leaching of free Levofloxacin from the coating, only tethered Levofloxacin moieties remained eliminating the observation of a zone of inhibition.

Without being bound by theory, such a result may be due to greater solubility and, thus, greater diffusion of "free", i.e. untethered, Levofloxacin molecules in Example 3 as compared to Reference 2. For Reference 2, Levofloxacin crystallites were present within the coating (see FIG. 1). The Levofloxacin molecules within the crystallites would be unable to diffuse out of the coating resulting in an overall reduction in free, diffusible Levofloxacin. In contrast, for the tethered sample, a homogeneous dispersion of the Levofloxacin moieties was obtained which, due to the high hydrophilicity of the Levofloxacin moieties, would be expected to enhance the diffusion of water into the coating and the diffusion of Levofloxacin molecules from the coating.

Example 8

Coatings of the polysiloxane copolymer containing 5 wt % tethered Levofloxacin from Example 2A were prepared on aluminum discs with 250 μL of coating solution. The coating solution was prepared from 5 weight percent tethered Levofloxacin (3.8 g, 0.0145 eq. epoxy), in methanol (4.24 g), and DETA (311 μL, 0.0145 eq. N—H). The coating solution was applied to the aluminum disc with a pipette. The coated aluminum discs were allowed to dry under ambient conditions for 1 hr, and then were placed in an 80° C. oven for 1 hr.

A coating solution containing 5 wt % of physically blended, untethered (doped) Levofloxacin was from a solution of Levofloxacin (0.06 g, $1.8 \times 10^{-4}$ moles), glycidyl ether functional polysiloxane from Example 1 (1.2 g, 0.005 eq. epoxy) and DETA (107 μL, 0.005 eq. N—H), in 2.7 g chloroform. The coating was then applied to aluminum discs as above.

A coating solution which did not contain Levofloxacin (Control) was prepared as follows: glycidyl ether functional polysiloxane from Example 1 (1.2 g, 0.005 eq. epoxy and DETA (107 μL, 0.005 eq. N—H), in 2.8 g chloroform. The coating was then applied to aluminum discs as above.

Figure 6:
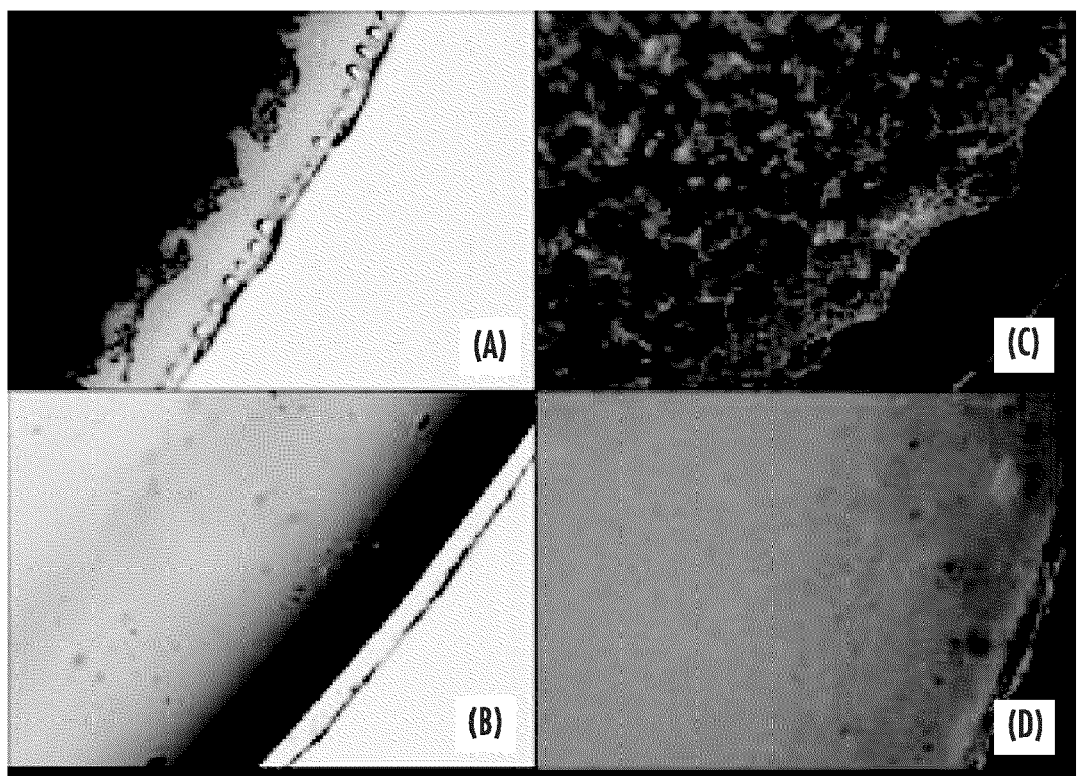
FIG. 6 shows optical [(a) and (b)] and fluorescence [(c) and (d)] microscopy images of coatings containing 1 wt % of doped [(a) and (c)] and tethered [(b) and (d)] Levofloxacin according to some embodiments.

Characterization of the morphology of these coatings was conducted using both optical and fluorescence microscopy. Since Levofloxacin fluoresces so strongly, tethered and doped samples were produced using 1 wt % Levofloxacin as opposed to the 5 wt % samples, to facilitate morphological characterization using fluorescence microscopy. As shown in FIG. 6, the Levofloxacin moieties, are uniformly distributed throughout the coating for the tethered coating, while the fluorescence for the doped coating was non-uniform. No fluorescence is observed at the outer edge of the doped sample, thereby indicating insolubility of the Levofloxacin in the coating matrix.

The coated samples were also immersed in a PBS solution for 28 days to determine of the Levofloxacin was leachable from the coating. After such immersion, the doped sample displayed no antimicrobial activity, but the tethered sample showed antimicrobial activity exclusively at the coating surface. This result suggests that the zone of inhibition observed for the tethered sample before immersion was most likely due to leaching of residual, unreacted Levofloxacin from the coating. After sufficient leaching of free Levofloxacin from the coating, only tethered Levofloxacin moieties remained, eliminating the observation of a zone of inhibition. The presence of some "free" or unreacted Levofloxacin in the Tethered sample is consistent with fourier-transform infrared spectroscopy results Antimicrobial activity of the 5 wt % coatings was determined as follows. The coated glass coverslips were inverted and placed on a Lauria-Bertani (LB) agar plate inoculated with the gram-negative bacterium, *Escherichia coli* (~$10^7$ cells mL$^{-1}$). A respiratory dye, 2,3,5-triphenyltetrazolium chloride (TTC), was incorporated into the LB agar (70 mg/L) to visualize the bacterial growth (red color). Agar plates with inverted coated discs were incubated for 48 hours at 37° C. and examined for both zones of growth inhibition and inhibition of growth on the coating surfaces.

Figure 7:
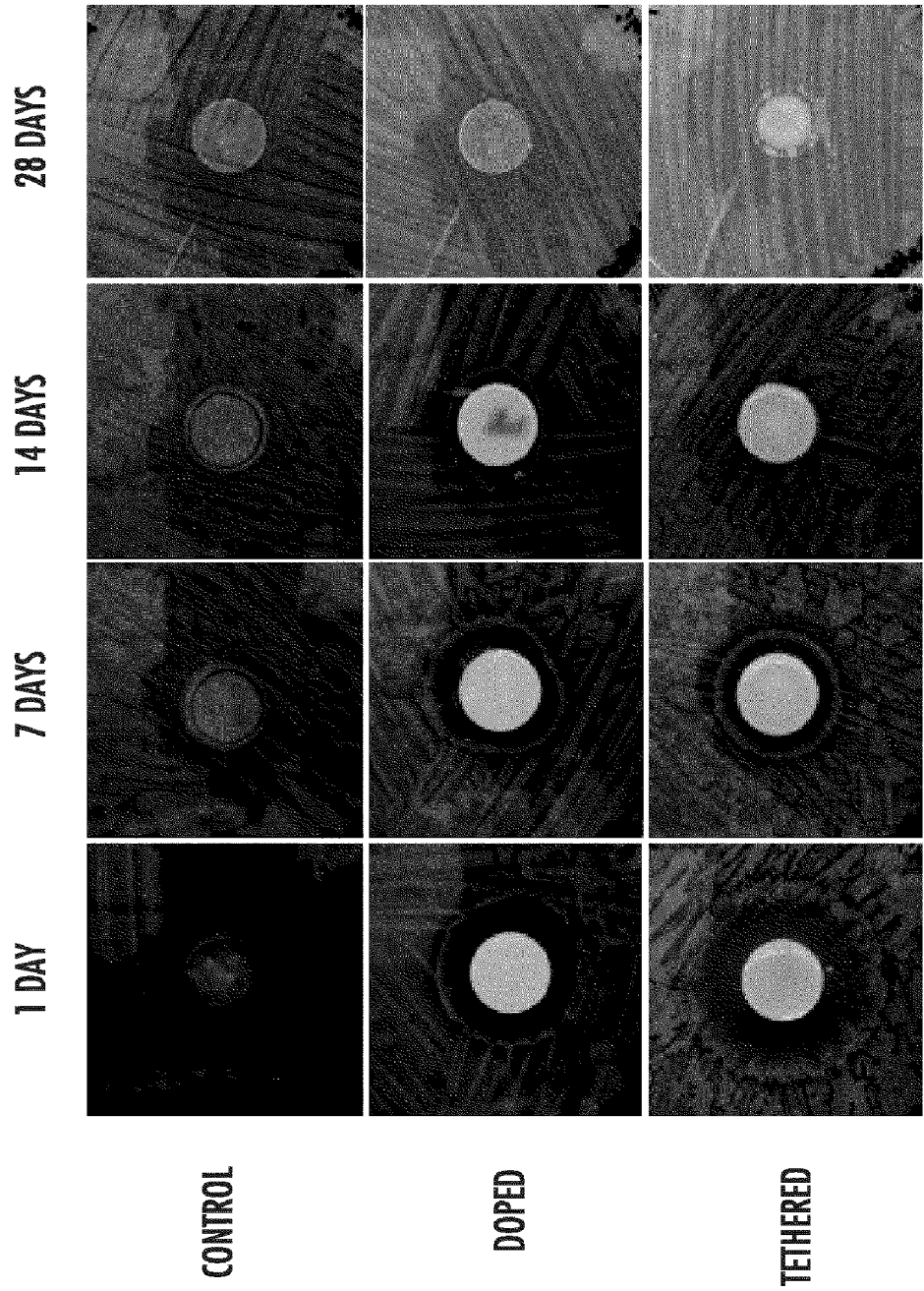
FIG. 7 is photographs of coated aluminum specimens with various Levofloxacin preparations (tethered and doped) and a control preparation, as tested for antimicrobial activity, in agar plates inoculated with *Escherichia coli*, after one day, seven days, fourteen days, and twenty eight days of preconditioning in PBS (phosphate buffered saline).

FIG. 7 illustrates the antimicrobial activity of the discs prepared according to Example 8. The control coating shows extensive microbial growth on the surface of the coating and no evidence of a zone of inhibition. In contrast, both the doped and tethered samples showed antimicrobial activity on the surface of the coating and a relatively large zone of inhibition. Interestingly, the zone of inhibition for the tethered sample was initially much larger than that for the Doped sample indicating greater Levofloxacin release from the tethered sample. This result may be due to differences in coating morphology and Levofloxacin dispersion. Considering the insolubility of Levofloxacin in the polysiloxane matrix and the low surface energy of polysiloxanes, the smaller zone of inhibition exhibited by the doped sample may be due to the generation of a coating surface morphology consisting of a largely polysiloxane-rich composition at the coating-air interface that is much lower in Levofloxacin than the bulk of the coating. Whereas, because Levofloxacin is covalently bound to the polysiloxane matrix for the tethered sample, Levofloxacin moieties must necessarily be in the vicinity of the coating-air interface thereby facilitating release from the coating.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While several, non-limiting examples have been illustrated and described, it should be understood that changes and modifications can be made therein in accordance with ordinary skill in the art without departing from the invention in its broader aspects as defined in the following claims.

What is claimed is:
1. A polymer formed by
(a) reaction of a polyhydrosiloxane of general formula

$$R^1R^2R^3SiO-(SiR^4R^5-O)_y(SiR^6H-O)_x(SiR^7R^8-O)_zSiR^9R^{10}R^{11}$$

with a reactive compound to provide a functionalized polysiloxane, wherein the reactive compound comprises (1) a first reactive group, which is capable of reacting with an Si—H group, at one end, and (2) a second reactive group, which is capable of reacting with a fluoroquinolone antibiotic, at its other end; and
the first reactive group comprises a vinylic group; and the second reactive group comprises an epoxy group or an anhydride group;
(b) reaction of the functionalized polysiloxane with a fluoroquinolone antibiotic or a pharmaceutically acceptable salt thereof to provide a fluoroquinolone-functionalized polysiloxane;
wherein $R^1$, $R^2$, $R^3$, $R^4$, $R^5$, $R^6$, $R^8$, $R^9$, $R^{10}$, and $R^{11}$ are independently $C_1$-$C_{20}$ alkyl, benzyl, tolyl, xylyl, or phenyl;
$R^7$ is a $C_1$-$C_{20}$ alkyl, benzyl, tolyl, xylyl, phenyl, texturizing moiety, a cross-linkable group, or a combination thereof;
x is 1 to 100;
y is 0 to 100;
z is 0 to 100;
at least one of y and z is greater than 0; and
the polymer contains at least one fluoroquinolone group.

2. The polymer of claim 1, wherein the fluoroquinolone antibiotic is ofloxacin.

3. The polymer of claim 1, wherein the polyhydrosiloxane is selected from the group consisting of poly(methylhydro-co-dimethyl)siloxane, polymethylhydrosiloxane, polyethylhydrosiloxane, polyphenyl-(dimethylhydro) siloxane, methylhydrosiloxane-phenylmethylsiloxane copolymer, methylhydrosiloxane-octylmethylsiloxane copolymer, or blends of any two or more thereof.

4. The polymer of claim 1, wherein the reactive compound includes 3 to 20 carbon atoms.

5. The polymer of claim 1, wherein the reactive compound includes at least one ether linkage.

6. The polymer of claim 1, wherein the fluoroquinolone-functionalized polysiloxane includes at least one fluoroquinolone group linked to the polymer by a hydrolytically labile linkage.

7. The polymer of claim 1, wherein the cross-linkable group includes a pendent epoxy group, a pendent anhydride group, or a mixture thereof.

8. A coating composition comprising the polymer of claim 1.

9. A coating composition comprising the polymer of claim 7.

10. The polymer of claim 1, wherein $R^1$, $R^2$, $R^3$, $R^4$, $R^5$, $R^6$, $R^8$, $R^9$, $R^{10}$, and $R^{11}$ are methyl; and $R^7$ is methyl, a texturizing moiety, a cross-linkable group, or a combination thereof.

11. The polymer of claim 10, wherein the reactive compound comprises an allyl epoxy ether.

12. The polymer of claim 10, wherein the allyl epoxy ether comprises allyl glycidyl ether.

13. The polymer of claim 10, wherein the reactive compound includes a vinylic group and an anhydride group.

14. The polymer of claim 13, wherein the reactive compound is 7-(allyloxy)-4-methyl-2H-chromen-2-one, 3-(2-methylprop-1-enyl)dihydrofuran-2,5-dione, or cis-5-norbornene-endo-2,3-dicarboxylic anhydride.

15. The polymer of claim 10, wherein the reactive compound includes a vinylic group and an epoxy group.

16. The polymer of claim 15, wherein the reactive compound is 3-vinyl-7-oxabicyclo[4.1.0]heptane.

17. The polymer of claim 10, wherein the fluoroquinolone antibiotic is ofloxacin.

18. The polymer of claim 10, wherein the texturizing moiety includes a polyether group, a perfluoroalkyl group, or an alkoxy alkyl ester group.

19. The polymer of claim 10, wherein the polyhydrosiloxane has a weight average molecular weight of about 500 to 15,000 g/mol.

20. A fluoroquinolone-functionalized polysiloxane comprising at least one fluoroquinolone group, wherein the polysiloxane polymer is formed by a process which includes reaction of a reactive compound with a fluoroquinolone antibiotic and a polyhydrosiloxane of general formula

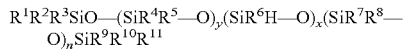

wherein $R^1$, $R^2$, $R^3$, $R^4$, $R^5$, $R^6$, $R^8$, $R^9$, $R^{10}$, and $R^{11}$ are independently $C_1$-$C_{20}$ alkyl;

$R^7$ is a $C_1$-$C_{20}$ alkyl, texturizing moiety, a cross-linkable group, or a combination thereof;

x is 1 to 100;
y is 0 to 100;
z is 0 to 100; and
at least one of y and z is greater than 0;

wherein the reactive compound comprises (1) a first reactive group, which is capable of reacting with an Si—H group, at one end, and (2) a second reactive group, which is capable of reacting with a fluoroquinolone antibiotic, at its other end; and the first reactive group is a vinylic group, and the second reactive group is an epoxy group or an anhydride group.

21. The fluoroquinolone-functionalized polysiloxane of claim 20, wherein $R^1$, $R^2$, $R^3$, $R^4$, $R^5$, $R^6$, $R^8$, $R^9$, $R^{10}$, and $R^{11}$ are methyl; $R^7$ is a methyl group, a texturizing moiety, a cross-linkable group, or a combination thereof; and the reactive compound includes 3 to 20 carbon atoms.

22. The fluoroquinolone-functionalized polysiloxane of claim 21, wherein the fluoroquinolone antibiotic is ofloxacin.

23. The fluoroquinolone-functionalized polysiloxane of claim 21, wherein the fluoroquinolone-functionalized polysiloxane includes at least one fluoroquinolone group linked by a hydrolytically labile linkage.

24. The fluoroquinolone-functionalized polysiloxane of claim 21, wherein the fluoroquinolone antibiotic is levofloxacin.

25. A coating composition comprising the fluoroquinolone-functionalized polysiloxane of claim 21.

* * * * *